(12) United States Patent
Davies

(10) Patent No.: US 9,737,540 B2
(45) Date of Patent: Aug. 22, 2017

(54) COMBINATION TREATMENT OF CANCER

(71) Applicant: ASTRAZENECA AB, Sodertalje (SE)

(72) Inventor: Barry Robert Davies, Macclesfield (GB)

(73) Assignee: ASTRAZENECA AB (SE)

(*) Notice: Subject to any disclaimer, the term of this patent is extended or adjusted under 35 U.S.C. 154(b) by 0 days.

(21) Appl. No.: 15/018,157

(22) Filed: Feb. 8, 2016

(65) Prior Publication Data

US 2016/0151373 A1   Jun. 2, 2016

Related U.S. Application Data

(63) Continuation of application No. 14/361,718, filed as application No. PCT/GB2012/052969 on Nov. 30, 2012, now abandoned.

(60) Provisional application No. 61/564,975, filed on Nov. 30, 2011.

(51) Int. Cl.
| | |
|---|---|
| *A61K 31/519* | (2006.01) |
| *A61K 31/4166* | (2006.01) |
| *A61K 31/277* | (2006.01) |
| *A61K 45/06* | (2006.01) |
| *A61K 31/5025* | (2006.01) |
| *A61K 31/58* | (2006.01) |

(52) U.S. Cl.
CPC .......... *A61K 31/519* (2013.01); *A61K 31/277* (2013.01); *A61K 31/4166* (2013.01); *A61K 31/5025* (2013.01); *A61K 31/58* (2013.01); *A61K 45/06* (2013.01)

(58) Field of Classification Search
IPC .......................... A61K 31/519,31/4166, 31/277
See application file for complete search history.

(56) References Cited

U.S. PATENT DOCUMENTS

| | | | |
|---|---|---|---|
| 5,439,686 A | 8/1995 | Desai et al. | |
| 6,162,804 A | 12/2000 | Bilodeau et al. | |
| 6,432,947 B1 | 8/2002 | Arnaiz et al. | |
| 6,749,868 B1 | 6/2004 | Desai et al. | |
| 2002/0094974 A1 | 7/2002 | Castelhano et al. | |
| 2003/0045536 A1 | 3/2003 | Castelhano et al. | |
| 2003/0073708 A1 | 4/2003 | Castelhano et al. | |
| 2003/0139427 A1 | 7/2003 | Castelhano et al. | |
| 2004/0014694 A1 | 1/2004 | Chakroun | |
| 2004/0082598 A1 | 4/2004 | Castelhano et al. | |
| 2004/0082599 A1 | 4/2004 | Castelhano et al. | |
| 2006/0111362 A1 | 5/2006 | Kira et al. | |
| 2006/0148844 A1 | 7/2006 | Nakade et al. | |
| 2007/0082838 A1 | 4/2007 | De et al. | |
| 2007/0117744 A1 | 5/2007 | Desai et al. | |
| 2007/0135402 A1 | 6/2007 | Habashita et al. | |
| 2008/0070936 A1 | 3/2008 | Castelhano et al. | |
| 2008/0108612 A1 | 5/2008 | Carrez et al. | |
| 2008/0119467 A1 | 5/2008 | Carrez et al. | |
| 2008/0161382 A1 | 7/2008 | Desai et al. | |
| 2008/0161404 A1 | 7/2008 | Carroll et al. | |

FOREIGN PATENT DOCUMENTS

| | | |
|---|---|---|
| EP | 0100172 B1 | 8/1987 |
| EP | 1444982 A1 | 8/2004 |
| GB | 1047935 A1 | 11/1966 |
| WO | WO 93/20097 A1 | 10/1993 |
| WO | WO 95/00516 A1 | 1/1995 |
| WO | WO 97/38665 A2 | 10/1997 |
| WO | WO 99/07703 A1 | 2/1999 |
| WO | WO 99/62908 A2 | 12/1999 |
| WO | WO 99/65909 A1 | 12/1999 |
| WO | WO 00/75145 A1 | 12/2000 |
| WO | WO 01/07050 A1 | 2/2001 |
| WO | WO 01/14371 A1 | 3/2001 |
| WO | WO 02/00661 A1 | 1/2002 |
| WO | WO 02/18348 A3 | 3/2002 |
| WO | WO 02/057267 A1 | 7/2002 |
| WO | WO 02/076484 A2 | 10/2002 |
| WO | WO 03/057696 A1 | 7/2003 |
| WO | WO 03/088908 A3 | 10/2003 |
| WO | WO 2004/014850 A3 | 2/2004 |
| WO | WO 2004/021979 A2 | 3/2004 |
| WO | WO 2004/043380 A3 | 5/2004 |
| WO | WO 2004/080463 A1 | 9/2004 |

(Continued)

OTHER PUBLICATIONS

Baskin-Bey (3rd European Multidisciplinary Meeting on Urological Cancers • Nov. 4-6, 2011 • Barcelona, Spain).*
Thomas et al ( Urology vol. 78, Issue 3, Supplement, Sep. 2011, pp. S293).*
Scher et al. Lancet. Apr. 24, 2010; 375(9724): 1437-1446.*
Attard et al. (Clinical Res. Published on line First Mar. 3, 2011).*
JAPIC Clinical Trials (Sep. 9, 2011).*
Goodman and Gilman $9^{th}$ edition (1996) p. 1225-1232.*
Bales et al; Use of F-FDG PET as a biomarker to demonstrate activity of the novel AKT inhibitor AZD5363 in a xenograft model; AACR; Apr. 4, 2011; p. 1030.
Bradley et al; Tumor Targeting by Covalent Conjugation of a Natural Fatty Acid to Paclitaxel; Clin. Cancer Res.; 2001; 7; pp. 3229-3238.
Barnett et al; The Akt/PKB Family of Protein Kinases: A Review of Small Molecule Inhibitors and Progress Towards Target Validation; Current Topics in Medicinal Chemistry; 2005; vol. 5; pp. 109-125.
Davies et al; Characterization of AZD5363, an orally bioavailable, potent ATP-competitive inhibitor of AKT kinases with pharmacodynamic and antitumor activity in preclinical models; AACR; Apr. 4, 2011; p. 4477.

(Continued)

*Primary Examiner* — Shirley V Gembeh
(74) *Attorney, Agent, or Firm* — Daniel Kopp

(57) ABSTRACT

The present invention relates to a combination comprising AZD5363, or a pharmaceutically acceptable salt thereof, and at least one androgen receptor signalling modulator selected from MDV-3100 (also known as enzalutamide), AZD3514, abiraterone (or an ester prodrug thereof: e.g. abiraterone acetate), and bicalutamide; or a pharmaceutically acceptable salt thereof. Each of these combinations may be useful in the treatment of cancer. The invention also relates to pharmaceutical compositions comprising such combinations, and further relates to methods of treatment comprising the simultaneous, sequential or separate administration of AZD5363, or a pharmaceutically acceptable salt thereof, with at least one androgen receptor signalling modulator as described above, to warm-blooded animal, such as a human for the treatment of cancer. The invention also relates to a kit comprising such combinations.

8 Claims, 3 Drawing Sheets

(56) References Cited

FOREIGN PATENT DOCUMENTS

| | | |
|---|---|---|
| WO | WO 2004/094426 A1 | 11/2004 |
| WO | WO 2005/003128 A1 | 1/2005 |
| WO | WO 2005/020921 A3 | 3/2005 |
| WO | WO 2005/026149 A1 | 3/2005 |
| WO | WO 2005/044181 A3 | 5/2005 |
| WO | WO 2005/051304 A3 | 6/2005 |
| WO | WO 2005/117909 A3 | 12/2005 |
| WO | WO 2006/046023 A1 | 5/2006 |
| WO | WO 2006/046024 A1 | 5/2006 |
| WO | WO 2006/071819 A1 | 7/2006 |
| WO | WO 2006/075094 A3 | 7/2006 |
| WO | WO 2006/075095 A3 | 7/2006 |
| WO | WO 2006/091450 A1 | 8/2006 |
| WO | WO 2006/124118 A1 | 11/2006 |
| WO | WO 2006/135639 A1 | 12/2006 |
| WO | WO 2007/007919 A2 | 1/2007 |
| WO | WO 2007/025090 A3 | 3/2007 |
| WO | WO 2007/084667 A3 | 7/2007 |
| WO | WO 2007/125320 A1 | 8/2007 |
| WO | WO 2007/125310 A3 | 11/2007 |
| WO | WO 2007/125315 A2 | 11/2007 |
| WO | WO 2007/125321 A3 | 11/2007 |
| WO | WO 2007/125325 A1 | 11/2007 |
| WO | WO 2008/075109 A1 | 6/2008 |
| WO | WO 2008/075110 A1 | 6/2008 |
| WO | WO 2008/079346 A1 | 7/2008 |
| WO | WO 2009/047563 A1 | 4/2009 |
| WO | WO 2010/092371 A1 | 8/2010 |

OTHER PUBLICATIONS

Godbole et al; New Insights into the Androgen-Targeted Therapies and Epigenetic Therapies in Prostate Cancer; Prostate Cancer; vol. 2011; Oct. 12, 2011; pp. 1-13; XP055057925.

Greenwood et al; In vitro mechanism of action of AZD5363, a novel AKT inhibitor, in breast and prostate cancer cell lines; AACR; Apr. 4, 2011; p. 1052.
Harbron; A flexible unified approach to the analysis of pre-clinical combination studies; Stat. in Med.; Jul. 20, 2010; vol. 29; pp. 1746-1756.
International Preliminary Report on Patentability for corresponding PCT Application No. PCT/GB2008/050925; mailed Apr. 22, 2010.
Lamoureux et al; AZD5363 a novel Akt inhibitor delays prostate cancer progression by inhibiting androgen-receptor activity; The Vancouver Prostate Centre and AstraZeneca; Apr. 4, 2011.
Luke et al; Discovery of AZD5363, in orally bioavailable, potent, ATP-competitive inhibitor of AKT kinases; AACR; Apr. 4, 2011; p. 4478.
Opposition filed against corresponding application in Dominican Republic; Patent Application No. P2010-0103; mailed Aug. 20, 2010.
Opposition filed against corresponding application in Ecuador; Patent Application No. SP-10-10093; mailed Oct. 13, 2010.
Opposition filed against corresponding application in Costa Rica; Patent Application No. 11.359; mailed Nov. 1, 2010.
Quintela et al; Pyrazolopyrimidines: synthesis, effect on histamine release from rat peritoneal mast cells and cytotoxic activity, Eur. J. Med. Chem.; 2001; vol. 36; pp. 321-332.
Mackay; Transforming Drug Discovery Innovative Platforms; Pfizer; 30 Nov. 30, 2006.
Thomas et al., 'Synergistic Targeting of PI3K/AKT Pathway and Androgen Receptor Axis Significantly Delays Castration-Resistant Prostate Cancer Progression In Vivo', Mol. Cancer Ther. (2013); vol. 12; No. 11; 2342-2355.
Baskin-Bey (3rd European Multidisciplinary Meeting on Urological Cancers• Nov. 4-6, 2011 •Barcelona, Spain).
Allard et al. (Clinical Res. Published on line First Mar. 3, 2011).
Goodman and Gilman 9th edition (1996) p. 1225-1232.

\* cited by examiner

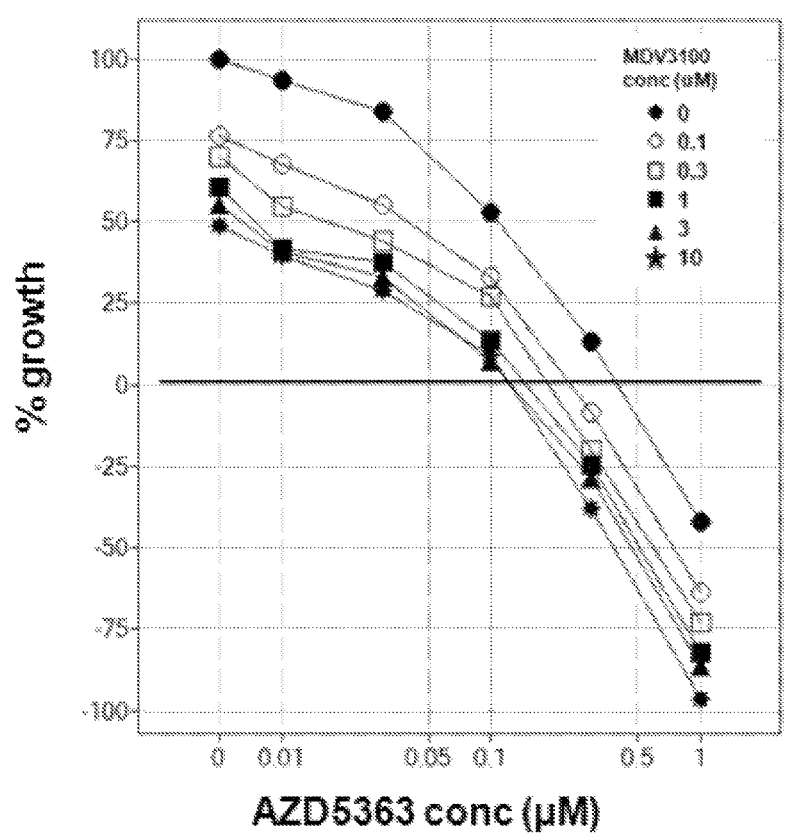
Figure 1: Inhibition of cell growth and enhanced cell death in LNCaP cells from combination use of AZD5363 with MDV3100

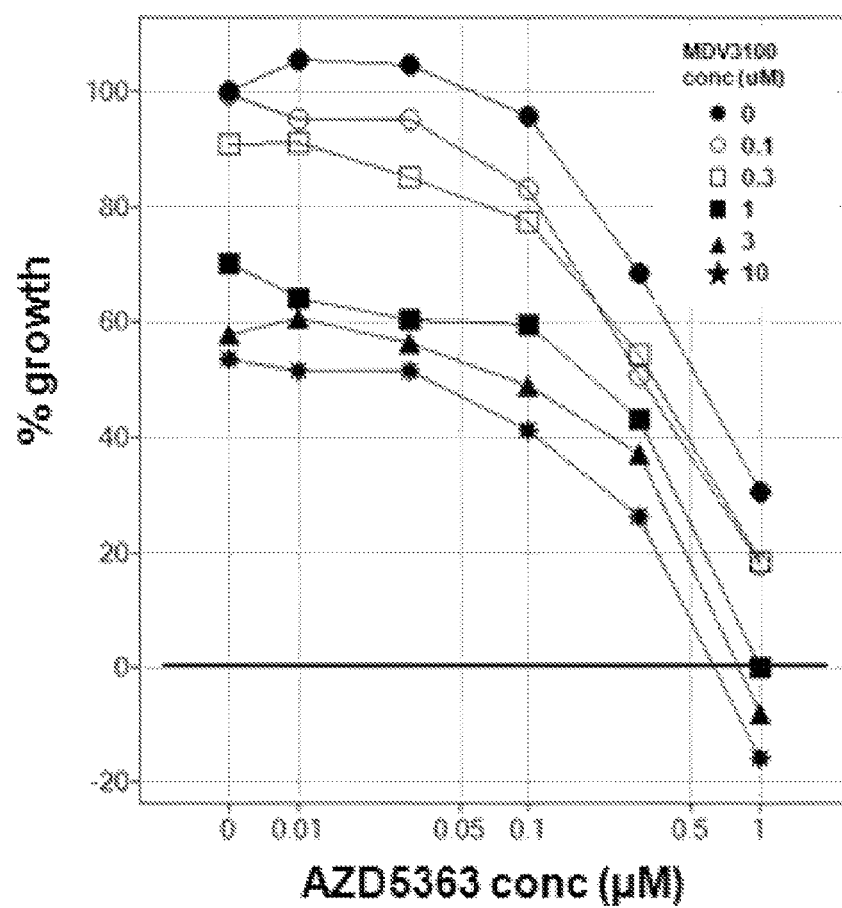
Figure 2: Inhibition of cell growth and enhanced cell death in VCAP cells from combination use of AZD5363 with MDV3100

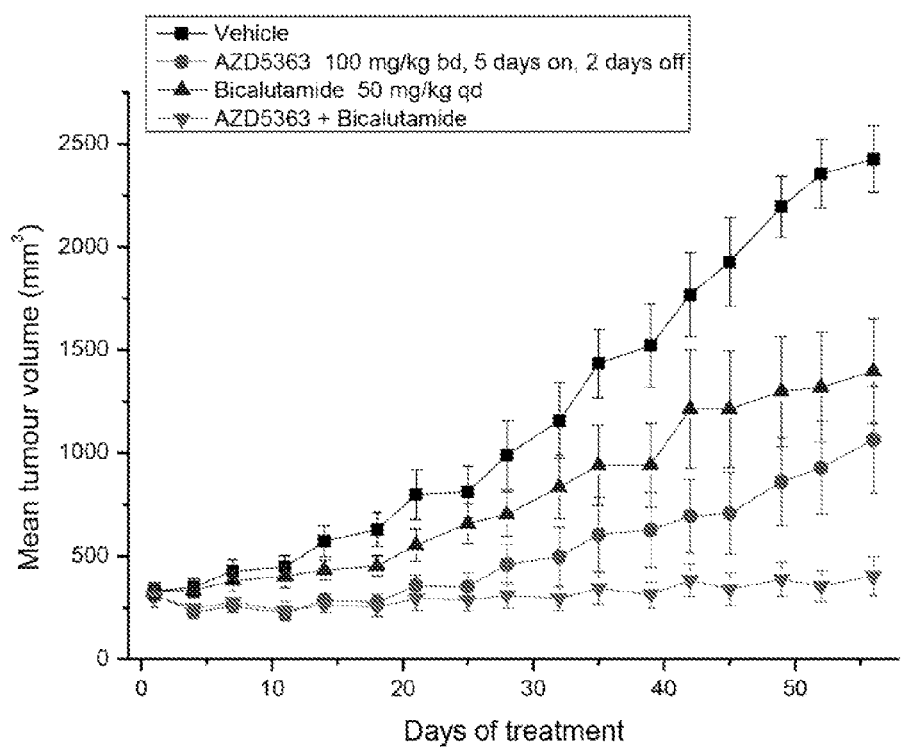
Figure 3: Enhanced anti-tumour efficacy in the LNCaP xenograft model from combination use of AZD5363 with bicalutamide

COMBINATION TREATMENT OF CANCER

This application is a Continuation of U.S. patent application Ser. No. 14/361,718, filed on May 30, 2014, which is a 35 U.S.C. §371 national stage entry of International Application No. PCT/GB2012/052969, filed Nov. 30, 2012, and claims priority under 35 U.S.C. §119(e) to U.S. provisional application Ser. No. 61/564975, filed Nov. 30, 2011, entitled "Combination Treatment", the contents of which are hereby incorporated by reference.

The present invention relates to a combination comprising (S)-4-amino-N-(1-(4-chlorophenyl)-3-hydroxypropyl)-1-(7H-pyrrolo[2,3-d]pyrimidin-4-yl)piperidine-4-carboxamide ("AZD5363"), or a pharmaceutically acceptable salt thereof, and at least one androgen receptor signalling modulator selected from 4-{3-[4-cyano-3-(trifluoromethyl)phenyl]-5,5-dimethyl-4-oxo-2-thioxoimidazolidin-1-yl}-2-fluoro-N-methylbenzamide ("MDV-3100", also known as enzalutamide), 1-{4-[2-(4-{1-[3-(trifluoromethyl)-7,8-dihydro[1,2,4]triazolo[4,3-b]pyrid-azin-6-yl]piperidin-4-yl}phenoxy)ethyl]piperazin-1-yl}ethanone ("AZD3514"), (3β-17-(pyridin-3-yl)androsta-5,16-dien-3-ol ("abiraterone", or an ester prodrug thereof: e.g. "abiraterone acetate") and N-[4-cyano-3-(trifluoromethyl)-phenyl]-3-[(4-fluorophenyl)-sulfonyl]-2-hydroxy-2-methylpropanamide ("bicalutamide"); or a pharmaceutically acceptable salt thereof. Each of these combinations may be useful in the treatment or prophylaxis of cancer. The invention also relates to pharmaceutical compositions comprising such combinations, and further relates to methods of treatment comprising the simultaneous, sequential or separate administration of AZD5363, or a pharmaceutically acceptable salt thereof, with at least one androgen receptor signalling modulator as described above, to warm-blooded animal, such as a human. The invention also relates to a kit comprising such combinations.

Cancer affects an estimated 10 million people worldwide. This figure includes incidence, prevalence and mortality. More than 4.4 million cancer cases are reported from Asia, including 2.5 million cases from Eastern Asia, which has the highest rate of incidence in the world. By comparison, Europe has 2.8 million cases, North America 1.4 million cases, and Africa 627,000 cases.

In the UK and US, for example, more than one in three people will develop cancer at some point in their life. Cancer mortality in the U.S. is estimated to account for about 600,000 a year, about one in every four deaths, second only to heart disease in percent of all deaths, and second to accidents as a cause of death of children 1-14 years of age. The estimated cancer incidence in the U.S. is now about 1,380,000 new cases annually, exclusive of about 900,000 cases of non-melanotic (basal and squamous cell) skin cancer.

Cancer is also a major cause of morbidity in the UK with nearly 260,000 new cases (excluding non-melanoma skin cancer) registered in 1997. Cancer is a disease that affects mainly older people, with 65% of cases occurring in those over 65. Since the average life expectancy in the UK has almost doubled since the mid nineteenth century, the population at risk of cancer has grown. Death rates from other causes of death, such as heart disease, have fallen in recent years while deaths from cancer have remained relatively stable. The result is that 1 in 3 people will be diagnosed with cancer during their lifetime and 1 in 4 people will die from cancer. In people under the age of 75, deaths from cancer outnumber deaths from diseases of the circulatory system, including ischaemic heart disease and stroke. In 2000, there were 151,200 deaths from cancer. Over one fifth (22%) of these were from lung cancer, and a quarter (26%) from cancers of the large bowel, breast and prostate.

Worldwide, the incidence and mortality rates of certain types of cancer (stomach, breast, prostate, skin, and so on) have wide geographical differences which are attributed to racial, cultural, and especially environmental influences. There are over 200 different types of cancer but the four major types, lung, breast, prostate and colorectal, account for over half of all cases diagnosed in the UK and US.

Current options for treating cancers include surgical resection, external beam radiation therapy and/or systemic chemotherapy. These are partially successful in some forms of cancer, but are not successful in others. There is a clear need for new and/or improved therapeutic treatments.

AZD5363 is disclosed amongst many other Examples in international patent application publication WO2009/047563. In this application it is stated that the compounds disclosed therein "may be applied as a sole therapy or may involve, in addition to a compound of the invention, conventional surgery, radiotherapy or chemotherapy". WO2009/047563 then lists many potential anti-tumour agents but nowhere in WO2009/047563 is there any mention of MDV-3100, AZD3514 or abiraterone, and nowhere is the specific combination of AZD5363 with bicalutamide disclosed.

Surprisingly, certain combinations according to the present invention may have particular benefit for the treatment of cancer, where a synergistic effect is observed when using the combination, when compared against the use of either combination partner alone.

According to the present invention a combination treatment may be considered to provide a synergistic effect if the effect is therapeutically superior, as measured by, for example, the extent of the response, the response rate, the time to disease progression or the survival period, to that achievable on dosing one or other of the components of the combination treatment at its conventional dose. For example, the effect of the combination treatment is synergistic if the use of the combination is superior to the effect achievable with AZD5363 or one of the specified combination partners, when used alone. Further, the effect of the combination treatment is synergistic if a beneficial effect is obtained in a group of patients that does not respond (or responds poorly) to AZD5363 or one of the specified combination partners, when used alone. In addition, the effect of the combination treatment may be considered to provide a synergistic effect if one of the components is dosed at its conventional dose and the other component(s) is/are dosed at a reduced dose and the therapeutic effect, as measured by, for example, the extent of the response, the response rate, the time to disease progression or the survival period, is equivalent to that achievable on dosing conventional amounts of the components of the combination treatment. In particular, synergy is deemed to be present if the conventional dose of AZD5363 or a specified combination partner may be reduced without detriment to one or more factors such as: extent of the response, the response rate, the time to disease progression and survival data, in particular without detriment to the duration of the response, but with fewer and/or less troublesome side-effects than those that occur when conventional doses of each component are used.

Furthermore, the effect of a combination treatment may be considered to provide a synergistic effect if one or both of the components may be dosed less frequently than the dosing schedule used for conventional dosing of each component when used alone, while not adversely impacting the beneficial effect otherwise achieved by the use of conventional amounts of an agent used alone. In particular, synergy is deemed to be present if the frequency of dosing of AZD5363 and/or a specified combination partner may be reduced relative to what would otherwise be conventional/ required when using one of the combination partners alone, without detriment to one or more factors such as: extent of the response, the response rate, the time to disease progression and survival data, in particular without detriment to the duration of the response, but with fewer and/or less troublesome side-effects than those that occur when conventional scheduling/doses of each component are used.

Surprisingly, according to the present invention, it has been found that the combination use of AZD5363 with certain specific androgen receptor signalling modulators provides a synergistic effect and may therefore provide an improved method of treating cancer.

Therefore, in the first aspect of the invention there is provided a combination comprising:
AZD5363, or a pharmaceutically acceptable salt thereof; with an androgen receptor signalling modulator selected from:
MDV-3100;
AZD3514;
abiraterone, or an ester prodrug thereof; and
bicalutamide;
or a pharmaceutically acceptable salt thereof.

A pharmaceutically acceptable salt is, for example, an acid-addition salt with an inorganic or organic acid, for example hydrochloric acid, hydrobromic acid, sulphuric acid, phosphoric acid, trifluoroacetic acid, citric acid or maleic acid.

In any aspect, embodiment or claim herein, an ester prodrug of abiraterone may be a compound where a $C_{1-6}$alkanoyl group is attached to the hydroxyl group of abiraterone. In any aspect, embodiment or claim herein, an ester prodrug of abiraterone may be a compound where a $C_{1-3}$alkanoyl group is attached to the hydroxyl group of abiraterone. In any aspect, embodiment or claim herein, an ester prodrug of abiraterone may be a compound where a $C_2$alkaloyl group is attached to the hydroxyl group of abiraterone (i.e. abiraterone acetate).

Herein, where the term "combination" is used it is to be understood that this may refer to simultaneous, separate or sequential administration of the components of the combination.
In one embodiment "combination" refers to simultaneous administration of the components of the combination.
In one embodiment "combination" refers to separate administration of the components of the combination.
In one embodiment "combination" refers to sequential administration of the components of the combination.

The above-mentioned embodiments may be combined with any one or combination of other aspect(s), claim(s) or embodiment(s) as defined herein, unless the context otherwise requires, to provide further aspects, embodiments and claims.

Where the administration is sequential or separate, the delay in administering the second component should not be such as to lose the benefit of the effect arising from use of the combination. Therefore, in one embodiment such sequential or separate treatment may involve the administration of each component of the combination within a period of 11 days.
In another embodiment this period is within 10 days.
In another embodiment this period is within 9 days.
In another embodiment this period is within 8 days.
In another embodiment this period is within 7 days.
In another embodiment this period is within 6 days.
In another embodiment this period is within 5 days.
In another embodiment this period is within 4 days.
In another embodiment this period is within 3 days.
In another embodiment this period is within 2 days.
In another embodiment this period is within 24 hours.
In another embodiment this period is within 12 hours.
In another embodiment this period is within 8 hours.
In another embodiment this period is within 6 hours.

It may be advantageous, within a given dosage cycle, to administer one specific component (A) of the combination before the other (B)—i.e. sequential dosing. Therefore, when sequential dosing is used with multiple consecutive dosage cycles, it naturally involves the dosage of A then B within a relatively short period, followed by a relatively longer period where neither component is dosed, before A then B are dosed again.

Therefore, in one embodiment the sequential administration comprises the sequential administration of AZD5363 prior to the administration of the other combination partner within a dosage cycle.

Herein, where "the other combination partner" is mentioned, unless the context otherwise requires, this refers to MDV-3100; AZD3514; abiraterone, or an ester prodrug thereof; or bicalutamide; in order to provide a range of further embodiments of the invention.

In another embodiment the sequential administration comprises the sequential administration of 'the other combination partner' (as defined above) prior to the administration of AZD5363 with a dosage cycle.

Dosage cycles may be separated by a number of days where none of the active combination components are administered.

In one embodiment there is provided a combination comprising:
AZD5363, or a pharmaceutically acceptable salt thereof; with an androgen receptor signalling modulator selected from:
MDV-3100;
AZD3514;
abiraterone, or abiraterone acetate; and
bicalutamide;
or a pharmaceutically acceptable salt thereof.

In one embodiment there is provided a combination comprising:
AZD5363, or a pharmaceutically acceptable salt thereof; with an androgen receptor signalling modulator selected from:
MDV-3100;
AZD3514;
abiraterone acetate; and
bicalutamide;
or a pharmaceutically acceptable salt thereof.

In one embodiment there is provided a combination comprising:
AZD5363, or a pharmaceutically acceptable salt thereof; with an androgen receptor signalling modulator selected from:
MDV-3100;
AZD3514;
abiraterone; and
bicalutamide;
or a pharmaceutically acceptable salt thereof.

In one embodiment there is provided a combination comprising AZD5363, or a pharmaceutically acceptable salt thereof; with MDV-3100.

In one embodiment there is provided a combination comprising AZD5363 with MDV-3100.

In one embodiment there is provided a combination comprising AZD5363, or a pharmaceutically acceptable salt thereof, with AZD3514, or a pharmaceutically acceptable salt thereof.

In one embodiment there is provided a combination comprising AZD5363 with AZD3514.

In one embodiment there is provided a combination comprising AZD5363, or a pharmaceutically acceptable salt thereof; with abiraterone or an ester prodrug thereof; or a pharmaceutically acceptable salt thereof.

In one embodiment there is provided a combination comprising AZD5363, or a pharmaceutically acceptable salt thereof; with abiraterone or abiraterone acetate.

In one embodiment there is provided a combination comprising AZD5363, or a pharmaceutically acceptable salt thereof with abiraterone.

In one embodiment there is provided a combination comprising AZD5363, or a pharmaceutically acceptable salt thereof; with abiraterone acetate.

In one embodiment there is provided a combination comprising AZD5363; with abiraterone or abiraterone acetate.

In one embodiment there is provided a combination comprising AZD5363, or a pharmaceutically acceptable salt thereof; with bicalutamide.

In one embodiment there is provided a combination comprising AZD5363; with bicalutamide.

In this specification any number of aspects or embodiments stated herein may be combined in any combination with each other (unless the context otherwise requires) to provide additional embodiments of the invention.

Where cancer is referred to, it may refer to oesophageal cancer, myeloma, hepatocellular cancer, pancreatic cancer, cervical cancer, ewings tumour, neuroblastoma, kaposis sarcoma, ovarian cancer, breast cancer, colorectal cancer, prostate cancer, bladder cancer, melanoma, lung cancer-non small cell lung cancer (NSCLC), and small cell lung cancer (SCLC), gastric cancer, head and neck cancer, brain cancer, renal cancer, lymphoma and leukaemia.

In one embodiment the cancer may be prostate cancer.

In one embodiment the cancer is hormone sensitive prostate cancer.

In one embodiment the cancer is castrate-resistant prostate cancer.

In one embodiment the cancer is non-metastatic castrate-resistant prostate cancer.

In another embodiment the cancer is in a metastatic state.

Therefore, in one embodiment the cancer is metastatic castrate-resistant prostate cancer.

In a further embodiment of the invention, the cancer is in a non-metastatic state.

Therefore, in one embodiment the cancer is non-metastatic castrate-resistant prostate cancer.

AZD5363 may be prepared according to the procedures described in WO2009/047563. MDV-3100 may be prepared according the procedures described in WO2006/124118. AZD3514 and pharmaceutically acceptable salts thereof may be prepared according to the procedures described in WO2010/092371. Abiraterone may be prepared according to the procedures described in WO1993/20097. Ester prodrugs of abiraterone such as abiraterone acetate may be prepared from abiraterone using esterification conditions and reagents that are well-known to the skilled person. Bicalutamide may be prepared according to the procedures described in EP0100172.

According to the present invention, there is provided a combination which comprises AZD5363, or a pharmaceutically acceptable salt thereof and MDV-3100 for use as a medicament.

According to the present invention, there is provided a combination which comprises AZD5363, or a pharmaceutically acceptable salt thereof; and AZD3514, or a pharmaceutically acceptable salt thereof; for use as a medicament.

According to the present invention, there is provided a combination which comprises AZD5363, or a pharmaceutically acceptable salt thereof; and abiraterone, or a pharmaceutically acceptable salt thereof; for use as a medicament.

According to the present invention, there is provided a combination which comprises AZD5363, or a pharmaceutically acceptable salt thereof; and abiraterone acetate, or a pharmaceutically acceptable salt thereof; for use as a medicament.

According to the present invention, there is provided a combination which comprises AZD5363, or a pharmaceutically acceptable salt thereof; and abiraterone or abiraterone acetate; or a pharmaceutically acceptable salt thereof; for use as a medicament.

According to the present invention, there is provided a combination which comprises AZD5363, or a pharmaceutically acceptable salt thereof; and bicalutamide; for use as a medicament.

According to a further aspect of the invention there is provided a pharmaceutical composition which comprises AZD5363, or a pharmaceutically acceptable salt thereof; and MDV-3100; in association with a pharmaceutically acceptable diluent or carrier.

According to a further aspect of the invention there is provided a pharmaceutical composition which comprises AZD5363, or a pharmaceutically acceptable salt thereof; and AZD3514, or a pharmaceutically acceptable salt thereof; in association with a pharmaceutically acceptable diluent or carrier.

According to a further aspect of the invention there is provided a pharmaceutical composition which comprises AZD5363, or a pharmaceutically acceptable salt thereof; and abiraterone, or a pharmaceutically acceptable salt thereof; in association with a pharmaceutically acceptable diluent or carrier.

According to a further aspect of the invention there is provided a pharmaceutical composition which comprises AZD5363, or a pharmaceutically acceptable salt thereof; and abiraterone acetate, or a pharmaceutically acceptable salt thereof; in association with a pharmaceutically acceptable diluent or carrier.

In one embodiment there is provided a pharmaceutical product comprising:
(i) a pharmaceutical composition which comprises AZD5363, or a pharmaceutically acceptable salt thereof, in association with a pharmaceutically acceptable diluent or carrier; and
(ii) a pharmaceutical composition which comprises 'the other combination partner', or a pharmaceutically acceptable salt thereof, in association with a pharmaceutically acceptable diluent or carrier.

As already specified hereinabove, where "the other combination partner" is mentioned, unless the context otherwise requires, this refers to one of MDV-3100; AZD3514; abiraterone, or an ester prodrug thereof (e.g. abiraterone acetate); or bicalutamide, to provide a range of further specific embodiments of the invention.

In one aspect there is provided a method of treating cancer, in a warm-blooded animal, such as a human, which comprises administering to said animal an effective amount of AZD5363, or a pharmaceutically acceptable salt thereof, in combination with an effective amount of 'the other combination partner' (as defined above), or a pharmaceutically acceptable salt thereof.

In one aspect where the treatment of cancer is indicated, it is to be understood that this may refer to the prevention of metastases and the treatment of metastases, i.e. cancer spread.

Therefore the combination of the present invention might be used to treat a patient who has no metastases to stop them occurring, or to lengthen the time period before they occur, and to a patient who already has metastases to treat the metastases themselves. Furthermore the treatment of cancer may refer to treatment of an established primary tumour or tumours and developing primary tumour or tumours.

Therefore, in one aspect the treatment of cancer relates to the prevention of metastases.

In another aspect of the invention the treatment of cancer relates to the treatment of metastases.

In another aspect of the invention the treatment of cancer relates to treatment of an established primary tumour or tumours or developing primary tumour or tumours.

In one embodiment the treatment of cancer relates to the treatment of primary cancer and metastases.

Herein, the treatment of cancer may refer to the prevention of cancer per se.

According to a further aspect of the invention, there is provided a kit comprising AZD5363, or a pharmaceutically acceptable salt thereof and 'the other combination partner' (as defined above), or a pharmaceutically acceptable salt thereof; optionally with instructions for use.

According to a further aspect of the invention, there is provided a kit comprising:
a) AZD5363, or a pharmaceutically acceptable salt, in a first unit dosage form;
b) 'the other combination partner' (as defined above), or a pharmaceutically acceptable salt thereof, in a second unit dosage form;
c) container means for containing said first and second dosage forms; and optionally
d) instructions for use.

An example of a unit dosage from might be a tablet for oral administration.

According to a further aspect of the invention there is provided a pharmaceutical composition which comprises AZD5363, or a pharmaceutically acceptable salt thereof; and 'the other combination partner' (as defined above), or a pharmaceutically acceptable salt thereof; in association with a pharmaceutically acceptable diluent or carrier, for use in the treatment of cancer.

According to a further aspect of the invention there is provided a pharmaceutical composition which comprises AZD5363, or a pharmaceutically acceptable salt thereof, in association with a pharmaceutically acceptable diluent or carrier; in combination with a pharmaceutical composition which comprises 'the other combination partner' (as defined above), or a pharmaceutically acceptable salt thereof, in association with a pharmaceutically acceptable diluent or carrier, for use in the treatment of cancer.

The pharmaceutical compositions may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a conventional manner using conventional excipients.

According to a further aspect of the present invention there is provided a kit comprising AZD5363, or a pharmaceutically acceptable salt thereof; and 'the other combination partner' (as defined above) or a pharmaceutically acceptable salt thereof; optionally with instructions for use; for use in the treatment of cancer.

According to a further aspect of the present invention there is provided a kit comprising:
a) AZD5363, or a pharmaceutically acceptable salt thereof, in a first unit dosage form;
b) 'the other combination partner' (as defined above), or a pharmaceutically acceptable salt thereof, in a second unit dosage form; and
c) container means for containing said first and second dosage forms; and optionally
d) instructions for use;
for use in the treatment of cancer.

According to another feature of the invention there is provided the use of AZD5363, or a pharmaceutically acceptable salt thereof, in combination with 'the other combination partner' (as defined above) or a pharmaceutically acceptable salt thereof, in the manufacture of a medicament for the treatment of cancer.

It may be convenient or medically appropriate for a physician to determine the exact dosage and scheduling for use of a combination product, such that the active components of the combination product may necessarily not be present together within a single dosage form at a fixed dose. Therefore a physician or pharmacist may prepare a combination medicament comprising the active combination products in readiness for simultaneous, separate or sequential combination use in medicine, for example to treat cancer in a warm-blooded animal, such as human.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for use in medicine.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for simultaneous, separate or sequential combination use in medicine.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for simultaneous, separate or sequential combination use for the treatment of cancer.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for simultaneous, separate or sequential combination use for the treatment of cancer in a warm-blooded animal such as a human.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for separate combination use for the treatment of cancer in a warm-blooded animal such as a human.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for sequential combination use for the treatment of cancer in a warm-blooded animal such as a human.

According to another feature of the invention there is provided the use of AZD5363, or a pharmaceutically acceptable salt thereof, in combination with 'the other combination partner' (as defined above) or a pharmaceutically acceptable salt thereof, in the preparation of a combination medicament for the treatment of cancer.

Therefore there is provided the use of AZD5363, or a pharmaceutically acceptable salt thereof, in combination with 'the other combination partner' (as defined above) or a pharmaceutically acceptable salt thereof, in the manufacture of a medicament for the treatment of cancer, in a warm-blooded animal, such as a human.

According to a further aspect of the present invention there is provided a combination comprising AZD5363, or a pharmaceutically acceptable salt thereof, and 'the other combination partner' (as defined above) or a pharmaceutically acceptable salt thereof, for use in the treatment of cancer.

In one embodiment there is provided AZD5363, or a pharmaceutically acceptable salt thereof, and 'the other combination partner' (as defined above) or a pharmaceutically acceptable salt thereof, for use in the treatment of cancer in a warm-blooded animal such as a human.

In one embodiment there is provided AZD5363, or a pharmaceutically acceptable salt thereof, and 'the other combination partner' (as defined above) or a pharmaceutically acceptable salt thereof, for use in the treatment of cancer in a warm-blooded animal such as a human wherein the AZD5363, or a pharmaceutically acceptable salt thereof, and 'the other combination partner' (as defined above) or a pharmaceutically acceptable salt thereof are administered simultaneously, separately or sequentially to the warm-blooded animal.

According to a further aspect of the present invention there is provided a combination treatment comprising the administration (simultaneous, separate or sequential) of an effective amount of AZD5363, or a pharmaceutically acceptable salt thereof, optionally together with a pharmaceutically acceptable diluent or carrier, and an effective amount of 'the other combination partner' (as defined above) or a pharmaceutically acceptable salt thereof, optionally together with a pharmaceutically acceptable diluent or carrier, to a warm-blooded animal, such as a human, in need of such therapeutic treatment, for the treatment of cancer.

The compositions of the invention may be obtained by conventional procedures using conventional pharmaceutical excipients, well known in the art. Thus, compositions intended for oral use may contain, for example, one or more colouring, sweetening, flavouring and/or preservative agents.

A compound such as AZD5363 may normally be administered to a warm-blooded animal at a unit dose within the range 5-5000 mg/m$^2$ body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed, for example 4-7 mg/kg twice daily. However the daily dose will necessarily be varied depending upon the host treated, the particular route of administration, and the severity of the illness being treated. Accordingly the practitioner who is treating any particular patient may determine the optimum dosage. For example, a pharmaceutical composition of the present invention suitable for oral administration could comprise 1-200 mg/mL of AZD5363 in 0.5% hydroxypropylmethylcellulose (HPMC). An alternative pharmaceutical dosage form suitable for oral administration involves the use of AZD5363 alone as a crystalline powder, within a standard capsule.

In one embodiment the AZD5363 is dosed to a patient at 150-300 mg per day on the days when it is dosed.

In one embodiment the AZD5363 is dosed to a patient at 200-350 mg per day on the days when it is dosed.

In another embodiment the AZD5363 is dosed to a patient at 240-320 mg per day on the days when it is dosed.

In another embodiment the AZD5363 is dosed to a patient at 320-400 mg per day on the days when it is dosed.

In one embodiment the AZD5363 is dosed to a patient at 300-500 mg per day on the days when it is dosed.

In one embodiment the AZD5363 is dosed to a patient at 320-480 mg per day on the days when it is dosed.

In one embodiment the AZD5363 is dosed to a patient at 300-650 mg per day on the days when it is dosed.

In one embodiment the AZD5363 is dosed to a patient at 350-600 mg per day on the days when it is dosed.

In one embodiment the AZD5363 is dosed to a patient at 300-1100 mg per day on the days when it is dosed.

In one embodiment the AZD5363 is dosed to a patient at 400-1000 mg per day on the days when it is dosed.

In one embodiment the AZD5363 is dosed to a patient at 150-300 mg per day on the days when it is dosed, and it is dosed every day of the week. (i.e. continuous dosing).

In one embodiment the AZD5363 is dosed to a patient at 200-350 mg per day on the days when it is dosed, and it is dosed every day of the week. (i.e. continuous dosing)

In one embodiment the AZD5363 is dosed to a patient at 240-320 mg per day on the days when it is dosed, and it is dosed every day of the week. (i.e. continuous dosing).

In another embodiment the AZD5363 is dosed to a patient at 320-400 mg per day on the days when it is dosed, and it is dosed for four consecutive days and then not dosed for 3 consecutive days thereafter within a seven day dosage cycle.

In one embodiment the AZD5363 is dosed to a patient at 300-500 mg per day on the days when it is dosed, and it is dosed for four consecutive days and then not dosed for 3 consecutive days thereafter within a seven day dosage cycle.

In one embodiment the AZD5363 is dosed to a patient at 320-480 mg per day on the days when it is dosed, and it is dosed for four consecutive days and then not dosed for 3 consecutive days thereafter within a seven day dosage cycle.

In one embodiment the AZD5363 is dosed to a patient at 300-650 mg per day on the days when it is dosed, and it is dosed for two consecutive days and then not dosed for five consecutive days thereafter within a seven day dosage cycle.

In one embodiment the AZD5363 is dosed to a patient at 350-600 mg per day on the days when it is dosed, and it is dosed for two consecutive days and then not dosed for five consecutive days thereafter within a seven day dosage cycle.

In one embodiment the AZD5363 is dosed to a patient at 300-1100 mg per day on the days when it is dosed, and it is dosed for two consecutive days and then not dosed for five consecutive days thereafter within a seven day dosage cycle.

In one embodiment the AZD5363 is dosed to a patient at 400-1000 mg per day on the days when it is dosed, and it is dosed for two consecutive days and then not dosed for five consecutive days thereafter within a seven day dosage cycle.

The 'other combination partner' (as defined above) will normally be administered (i.e. dosed) to a warm-blooded animal at a unit dose, of an amount known to the skilled practitioner as a therapeutically effective dose. For a single dosage form, the active ingredients may be compounded with an appropriate and convenient amount of excipients which may vary from about 5 to about 98 percent by weight of the total composition. Dosage unit forms will generally contain about 20 mg to about 500 mg of each active ingredient. However the daily dose will necessarily be varied depending upon the host treated, the particular route of administration, and the severity of the illness being treated. Accordingly the optimum dosage may be determined by the practitioner who is treating any particular patient.

The dosage of each of the drugs and their proportions have to be composed so that the best possible treatment effects, as defined by national and international guidelines (which are periodically reviewed and re-defined), will be met.

In one embodiment (when the "other combination partner" is abiraterone acetate) the abiraterone acetate is dosed orally to a patient at 750-1250 mg per day on the days when it is dosed.

In one embodiment (when the "other combination partner" is abiraterone acetate) the abiraterone acetate is dosed orally to a patient at 450-1250 mg per day on the days when it is dosed.

In one embodiment (when the "other combination partner" is abiraterone acetate) the abiraterone acetate is dosed orally to a patient at 450-1250 mg per day on the days when it is dosed, and it is dosed every day of the week. (i.e. continuous dosing).

In one embodiment (when the "other combination partner" is abiraterone acetate) the abiraterone acetate is dosed orally to a patient at 750-1250 mg per day on the days when it is dosed, and it is dosed every day of the week. (i.e. continuous dosing).

In another embodiment (when the "other combination partner" is abiraterone acetate), the abiraterone acetate is dosed orally to a patient at 800-1200 mg per day on the days when it is dosed.

In another embodiment (when the "other combination partner" is abiraterone acetate), the abiraterone acetate is dosed orally to a patient at 800-1200 mg per day on the days when it is dosed, and it is dosed every day of the week. (i.e. continuous dosing).

In another embodiment (when the "other combination partner" is abiraterone acetate), the abiraterone acetate is dosed orally to a patient at 900-1100 mg per day on the days when it is dosed.

In another embodiment (when the "other combination partner" is abiraterone acetate), the abiraterone acetate is dosed orally to a patient at 900-1100 mg per day on the days when it is dosed, and it is dosed every day of the week. (i.e. continuous dosing).

In further embodiments (when the "other combination partner" is abiraterone acetate), the patient is also dosed with a therapeutically effective amount of prednisone. Such dosing of prednisone may occur every day of the week. A therapeutically effective amount of prednisone may be from 5-20 mg per day. (e.g. a total of 10 mg per day).

In other embodiments (when the "other combination partner" is abiraterone acetate), the patient is not being treated with prednisone at the same time.

In one embodiment (when the "other combination partner" is MDV-3100), the MDV-3100 is dosed orally to a patient at 140-180 mg per day on the days when it is dosed.

In another embodiment (when the "other combination partner" is MDV-3100), the MDV-3100 is dosed orally to a patient at 150-170 mg per day on the days when it is dosed.

In one embodiment (when the "other combination partner" is MDV-3100), the MDV-3100 is dosed orally to a patient at 140-180 mg per day on the days when it is dosed and, it is dosed every day of the week. (i.e. continuous dosing).

In another embodiment (when the "other combination partner" is MDV-3100), the MDV-3100 is dosed orally to a patient at 150-170 mg per day on the days when it is dosed, and it is dosed every day of the week. (i.e. continuous dosing).

LIST OF FIGURES

FIG. 1: Inhibition of cell growth and enhanced cell death in LNCaP cells from combination use of AZD5363 with MDV3100.

FIG. 2: Inhibition of cell growth and enhanced cell death in VCAP cells from combination use of AZD5363 with MDV3100.

FIG. 3: Enhanced anti-tumour efficacy in the LNCaP xenograft model from combination use of AZD5363 with bicalutamide.

FIG. 1 shows the mean % growth in LNCaP cells for each concentration of AZD5363, either as a monotherapy or in combination with five different concentrations of MDV-3100, in the range 0.1 $\mu$M to 10 $\mu$M (n=3). Positive values (0 to 100%) show anti-proliferative effects and negative values (0 to −100%) are for cell killing. These results demonstrate that AZD5363 can inhibit the growth of LNCaP cells and induce cell death as a monotherapy and this effect is synergistically enhanced by treatment with MDV-3100.

FIG. 2 shows the mean % growth in VCAP cells for each concentration of AZD5363, either as a monotherapy or in combination with five concentrations of MDV-3100, in the range 0.1 $\mu$M to 10 $\mu$M (n=3). Positive values (0 to 100%) show anti-proliferative effects and negative values (0 to −100%) are for cell killing. These results demonstrate that AZD5363 can inhibit the growth of VCAP cells as a monotherapy and this effect is synergistically enhanced by treatment with MDV-3100.

FIG. 3 shows the mean tumour volume in mice, when treated with monotherapy and combination therapy involving AZD5363 and bicalutamide. Although not explicit in the figure, the "AZD5363+bicalutamide" data shown in the figure involves the same dosage and scheduling as is shown in the figure for AZD5363 alone and for bicalutamide alone, i.e. 100 mg/kg bd 5 days on, 2 days off of AZD5363 in combination with bicalutamide 50 mg/kg bd.

EXPERIMENTAL DETAILS

Combination of AZD5363 with MDV-3100

The LNCaP and VCAP prostate tumour cell lines (American Tissue Culture Collection) were routinely cultured in RMPI supplemented with 10% FCS and 2 mM L-glutamine. To determine the effect of AZD5363 and MDV-3100, either as a monotherapy or in combination, on cell growth, a proliferation assay was performed using the Sytox Green endpoint to measure live cell number after 5 days. Briefly, LNCAP or VCAP cells were seeded in 384-well plates at a density of 1500 or 2500 cells per well, respectively, and left to adhere overnight. Cells were then dosed with increasing concentrations of AZD5363 (0.01-1 µM), MDV-3100 (0.1-10 µM) or a combination of each agent in a 6×6 matrix format. After 5-day exposure to compound, Sytox Green nucleic acid dye (Invitrogen) diluted in TBS-EDTA (TBS=Tris-buffered saline, EDTA=ethylenediaminetetraacetic acid) buffer was added to cells at a final concentration of 0.13 mmol/L and the number of dead cells detected using an Acumen Explorer. Cells were then permeabilised by the addition of saponin (0.03% final concentration, diluted in TBS-EDTA buffer), incubated overnight and a total cell count measured. The live cell count was then determined by subtracting the number of dead cells per well from the total number of cells. Pre-dose measurements were made to indicate the number of live cells at the start of the experiment (Tz) and thus an indication of whether the treatment regimen had resulted in cell death. The data is presented as % growth using the NCI formulae as follows:

$$[(\mathit{Ti}-\mathit{Tz})/(C-\mathit{Tz})] \times 100 \text{ for concentrations for which } \mathit{Ti} \geq \mathit{Tz}$$

$$[(\mathit{Ti}-\mathit{Tz})/\mathit{Tz}] \times 100 \text{ for concentrations for which } \mathit{Ti} < \mathit{Tz}.$$

Where, 'Tz' represents the number of live cells at time zero, 'C' represents the control growth and Ti' represents the number of live cells in the presence of each drug regimen. This formula gives a growth percentage from −100% to +100%. Negative scores are for cell killing and positive scores are for anti-proliferation. The data are presented in FIG. 1 and FIG. 2. Synergism of the drug combination was evaluated using a unified approach described by C. Harbron (Stat. Med. 2010 Jul. 20; 29(16): 1746-56).

Combination Indicies and p Values for the Three Experiments

A combination index of <1 indicates synergism. 'p values' relate to statistical significance.

| Cell line | Experiment | CI | p value |
| --- | --- | --- | --- |
| LNCaP | 1 | 0.38 | p < 0.0001 |
|  | 2 | 0.32 | p < 0.0001 |
|  | 3 | 0.51 | p = 0.0001 |
| VCAP | 1 | 0.47 | p = 0.0003 |
|  | 2 | 0.59 | p = 0.003 |
|  | 3 | 0.75 | p = 0.22 |

Combination of AZD5363 with Bicalutamide

Combination of AZD5363 with bicalutamide results in greater tumour growth inhibition than monotherapy in a xenograft model of castrate resistant prostate cancer in vivo: LNCaP prostate cancer cells (PTEN null, androgen receptor positive) were implanted into the flank of athymic male nude mice. Tumour growth and the concentration of Prostate Specific Antigen (PSA) in the serum were monitored. When the serum PSA exceeded 50 ng/mL, mice were castrated. The mice were randomized into groups and treatment commenced when the PSA concentration recovered to at least 50 ng/mL. AZD5363 monotherapy treatment (100 mg/kg bd, 5 days on, 2 days off) resulted in 56% inhibition of tumour volume, and bicalutamide monotherapy treatment (50 mg/kg qd), resulted in 42% inhibition of tumour volume. The combination was significantly more efficacious, and resulted in 85% inhibition of tumour volume. This data shows that combination of AZD5363 and the androgen antagonist bicalutamide is well tolerated and results in greater efficacy than the equivalent monotherapy doses of each compound. The results are shown in FIG. 3.

The invention claimed is:

1. A combination treatment comprising the simultaneous, separate or sequential administration of an effective amount of:
   AZD5363, or a pharmaceutically acceptable salt thereof, optionally together with a pharmaceutically acceptable diluent or carrier; and
   an effective amount of MDV-3100, optionally together with a pharmaceutically acceptable diluent or carrier,
   to a warm-blooded animal in need of such therapeutic treatment, for use in the treatment of cancer.

2. The combination treatment as claimed in claim 1, for the treatment of prostate cancer.

3. The combination treatment as claimed in claim 1 wherein the cancer is castrate-resistant prostate cancer.

4. The combination treatment as claimed in claim 1 wherein the cancer is metastatic castrate-resistant prostate cancer.

5. A combination treatment comprising the simultaneous, separate or sequential administration of an effective amount of:
   AZD5363, or a pharmaceutically acceptable salt thereof, optionally together with a pharmaceutically acceptable diluent or carrier; and
   an effective amount of bicalutamide, or a pharmaceutically acceptable salt thereof, optionally together with a pharmaceutically acceptable diluent or carrier,
   to a warm-blooded animal in need of such therapeutic treatment, for use in the treatment of cancer.

6. The combination treatment as claimed in claim 5, for the treatment of prostate cancer.

7. The combination treatment as claimed in claim 5, wherein the cancer is castrate-resistant prostate cancer.

8. The combination treatment as claimed in claim 5, wherein the cancer is metastatic castrate-resistant prostate cancer.

* * * * *